United States Patent [19]

Sato et al.

[11] 4,101,590

[45] Jul. 18, 1978

[54] PROCESS FOR SEPARATION AND PURIFICATION OF VINYLPHENOL

[75] Inventors: Mikio Sato, Chiba; Kinya Tawara, Sohka; Shinpachiro Iwaki, Kobe; Kohji Matsumoto, Saitama; Kenichi Sekine, Kuki, all of Japan

[73] Assignee: Maruzen Oil Co., Ltd., Osaka, Japan

[21] Appl. No.: 716,731

[22] Filed: Aug. 23, 1976

[51] Int. Cl.² .................. C07C 39/18; C07C 37/28
[52] U.S. Cl. ......................... 568/750; 568/756
[58] Field of Search ........... 260/624 B, 621 A, 624 A, 260/627 R, 621 B

[56] References Cited

U.S. PATENT DOCUMENTS

| | | | |
|---|---|---|---|
| 2,553,470 | 5/1951 | Pines et al. | 260/624 B |
| 2,578,206 | 12/1951 | Pines et al. | 260/624 B |
| 3,198,842 | 8/1965 | Berrigan | 260/624 B |
| 3,277,185 | 10/1966 | Eisenlohr et al. | 260/627 R |
| 3,285,973 | 11/1966 | Arai et al. | 260/627 R |
| 3,526,668 | 9/1970 | Starnes et al. | 260/624 A |

Primary Examiner—James O. Thomas, Jr.
Assistant Examiner—Werren B. Lone
Attorney, Agent, or Firm—Sughrue, Rothwell, Mion, Zinn and Macpeak

[57] ABSTRACT

A process for the separation and purification of vinylphenol which comprises contacting crude vinylphenol containing vinylphenol and impurities such as phenol, alkylphenols, vinylphenol polymers and hydrocarbons countercurrently with an aqueous alkali solution together with a specific organic solvent.

Vinylphenol obtained is useful as the raw material for the production of polyvinylphenol or a vinylphenol copolymer which is utilized as a thermoplastic resin, an ion exchange membrane, an adhesive, a glass fiber-reinforced composite or the like.

21 Claims, 9 Drawing Figures

U.S. Patent   July 18, 1978   Sheet 1 of 3   4,101,590
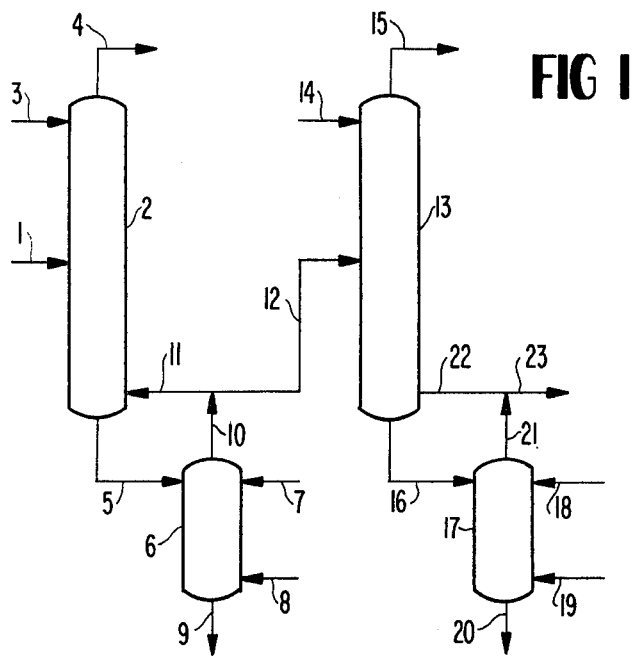
FIG 1
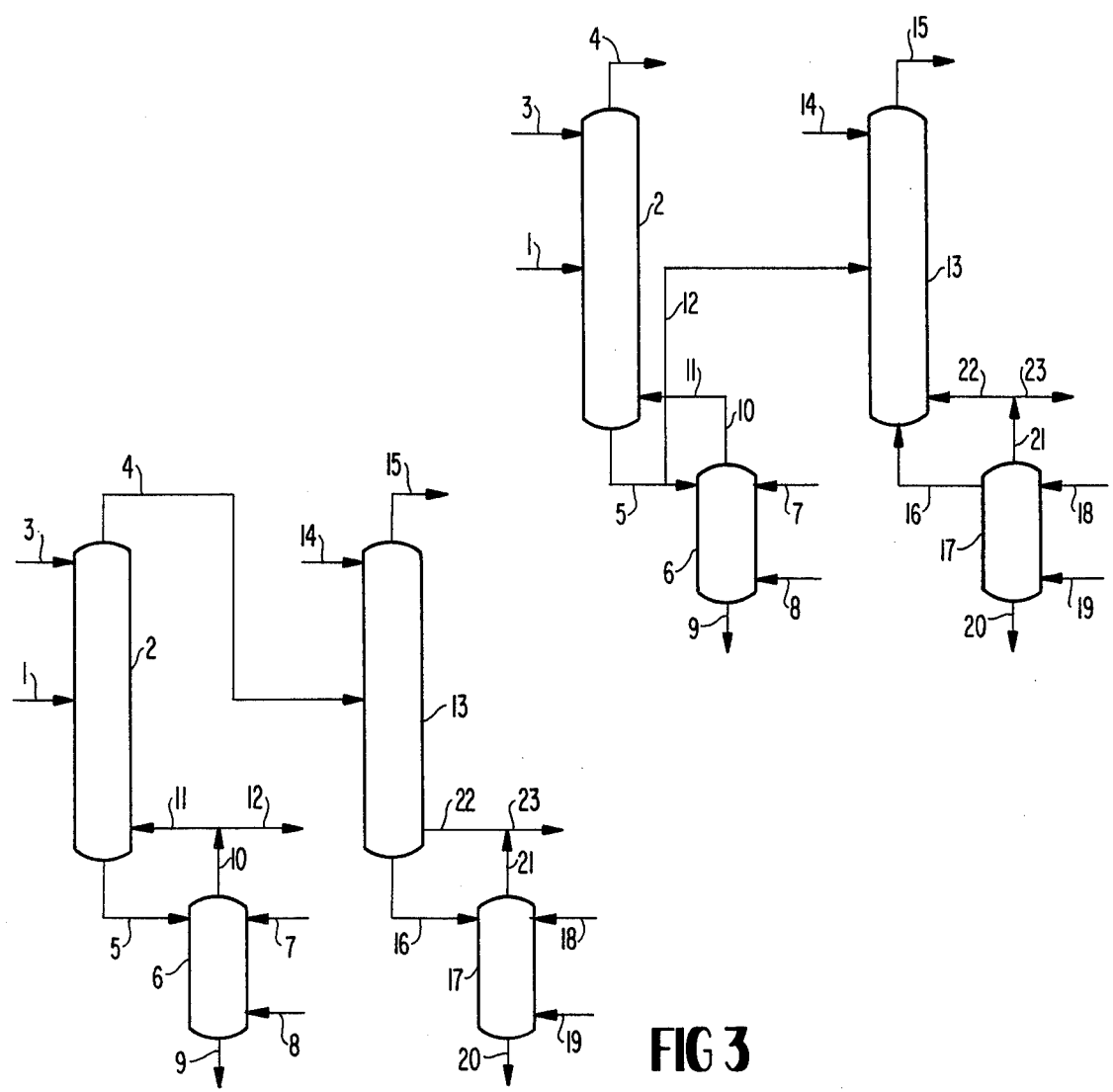
FIG 2
FIG 3

PROCESS FOR SEPARATION AND PURIFICATION OF VINYLPHENOL

BACKGROUND OF THE INVENTION

1. Field of the Invention

This invention relates to a process for the separation and purification of crude vinylphenol, and more specifically, to a process for the separation and purification of crude vinylphenol using an extracting procedure employing an aqueous alkali solution as an extracting agent with a specific organic solvent. For brevity, this extracting procedure will be referred to hereinafter as "an alkali extracting procedure" or simply as "an extracting procedure".

2. Description of the Prior Art

A number of methods for producing vinylphenol have been proposed and studied. These methods include, for example, a method involving recovering vinylphenol from a natural product, a method in which hydroxycinnamic acid is decomposed, a method wherein bis-(hydroxyphenyl) ethane is decomposed, a method in which ethylphenol is dehydrogenated, a method wherein o-coumaric acid is decomposed, and a method which comprises synthesizing acetoxystyrene from phenol and saponifying the acetoxystyrene. In all of these methods, the product obtained is crude vinylphenol containing vinylphenol and impurities such as hydrocarbons, alkylphenols, vinylphenol polymer and other phenols. For example, the product obtained by decomposing hydroxycinnamic acid contains impurities such as about 0 to 50% by weight of phenol, about 0 to 30% by weight of ethylphenol, about 0 to 5% by weight of vinylphenol polymer and about 0 to 105 by weight of unreacted hydroxycinnamic acid in addition to the vinylphenol. The product obtained by decomposing bis-(hydroxyphenyl) ethane contains about 0 to 50% by weight of phenol, about 0 to 20% by weight of ethylphenol and about 0 to 5% by weight of vinylphenol polymer. The product obtained by dehydrogenating ethylphenol contains about 0 to 10% by weight of phenol, about 0 to 90% by weight of ethylphenol, about 0 to 5% by weight of cresol, and about 0 to 5% by weight of vinylphenol polymer. The product obtained by decomposing o-coumaric acid contains about 0 to 10% by weight of phenol, about 0 to 30% by weight of ethylphenol, about 0 to 5% by weight of vinylphenol polymer, and about 0 to 10% by weight of unreacted o-coumaric acid. The product obtained by saponifying acetoxystyrene synthesized from phenol contains about 0 to 10% by weight of phenol, about 0 to 50% by weight of ethylphenol, and about 0 to 5% by weight of vinylphenol polymer. Therefore, purification of the crude vinylphenol so produced is essential.

To date, only one method has been reported for separating and purifying vinylphenol, which is a laboratory-scale purification of vinylphenol by recrystallization (B.B. Corson et. al.; J. Org. Chem. 23 548, 1958) However, poor separation and yields are obtained using this method and, hence, this method is not commercially feasible. Until now there has been no proposal of a method of separating and purifying vinylphenol which can be performed on a commercial scale with good efficiency.

SUMMARY OF THE INVENTION

Vinylphenol (ortho-, meta-or para-isomer) is a very unstable substance which tends to polymerize readily as compared with styrene, acrylic acid esters, etc. Since vinylphenol polymerizes immediately when subjected to an elevated temperature, if vinylphenol is purified using a method which requires heating, such as in distillation, the yield of vinylphenol is markedly reduced because of its polymerization.

An object of this invention is to provide a process for separating very unstable vinylphenol in high purity and in good yield from crude vinylphenol under stable operation while peventing any difficulty ascribable to the polymerization of vinylphenol during the separating procedure and to the vinylphenol polymer present in the crude vinylphenol.

Another object of this invention is to provide vinylphenol of high purity.

Another object of this invention is to provide a process for purifying highly pure vinyophenol from crude vinylphenol continuously for a long period.

These and other objects and avantages of this invention will become apparent from the following detailed description.

Extensive research has been made on a method of purifying crude vinylphenol containing vinylphenol which has the high tendency toward polymerization. As a result, it has now been found that very pure vinylphenol can be separated from crude vinylphenol in good yields using an extracting procedure comprising contacting crude vinylphenol countercurrently with an aqueous alkali solution as an extracting agent while the solute is being refluxed.

BRIEF DESCRIPTION OF THE DRAWINGS

FIGS. 1 to 9 are flowsheets showing embodiments of the process of this invention.

DETAILED DESCRIPTION OF THE INVENTION

Figure 4:
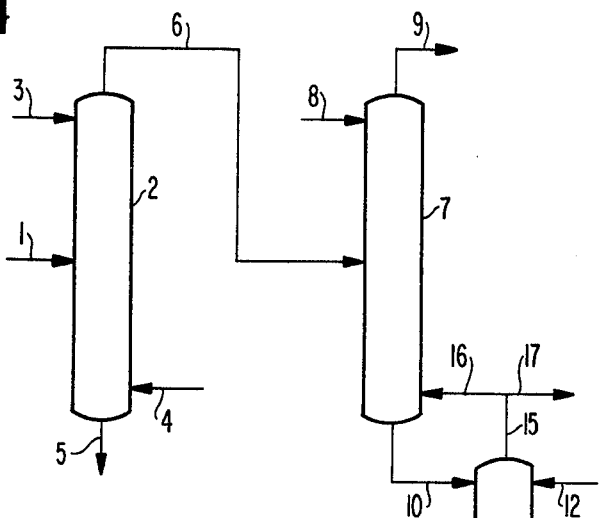

It is generally known to separate a mixture into its components by extraction with an alkali (to be referred to hereinafter for brevity as "alkali extraction") and a separation procedure utilizing the difference in acidity between the components. Since various phenols have acidity values which are very close to each other, sometimes even a mixture of two components cannot be separated into the components using an alkali extracting procedure. It was even unexpected prior to the present invention that only vinylphenol can be separated using an alkali extracting method from crude vinylphenol which contains alkylphenols (including ortho-, meta- and para-isomers) containing side chains with the same number of carbon atoms as vinylphenol and vinylphenol polymer.

The separation factors of the impurities contained in crude vinylphenol from vinylphenol, have been measured by us and the results obtained are shown in Table 1 below.

Table 1

| Separation Factors of Impurities with respect to p-Vinylphenol | |
|---|---|
| Impurities | Separation factor |
| o-Vinylphenol* | 1.3 |
| m-Vinylphenol* | 1.1 |
| Phenol | 0.05 |
| o-Ethylphenol | 6.3 |
| m-Ethylphenol | 6.4 |
| p-Ethylphenol | 6.2 |
| p-Cresol | 1.7 |
| n-Propylphenol | 44 |
| p-tert.-Butylphenol | 37 |
| Vinylphenol Polymer** | |

Table 1-continued

Separation Factors of Impurities with respect to p-Vinylphenol

| Impurities | Separation factor |
|---|---|
| (weight average molecular weight: about 5,000) | 0.004 |

*are not impurities but the desired products in this invention
**Although vinylphenol polymer is an impurity having a weak acidity, the vinylphenol polymer has a separation factor in alkali extraction of far less than 1 as is the case with more acidic impurities, and thus behaves in the alkali extraction as if it was a strongly acidic impurity.

The separation factor shown in Table 1 was calculated as follows:

A toluene solution of vinylphenol and one of the impurities (phenol, alkylphenols and vinylphenol polymer) and an aqueous solution of sodium hydroxide containing a lower number of mols than the total mols of the vinylphenol and the impurity contained in the toluene solution were placed in a separation funnel, and shaken thoroughly at 5° C. until extraction equilibrium was attained. After allowing the solution to stand, the contents of the vinylphenol and the impurity in the aqueous and organic phases were measured. The separation factor was thus calculated from the measured values using the following relationship.

$$\text{Separation Factor} = \frac{\frac{\text{Concentration of Vinylphenol in Aqueous Phase}}{\text{Concentration of Vinylphenol in Organic Phase}}}{\frac{\text{Concentration of Impurity in Aqueous Phase}}{\text{Concentration of Impurity in Organic Phase}}}$$

As a result of extensive and detailed work, the following information was obtained. The most important factor for determining the separation factor in alkali extraction is the difference in acidity. Vinylphenol has a slightly stronger acidity than ethylphenol or dimethylphenol having the same number of carbon atoms, and the separation factor of ethylphenol or dimethylphenol with respect to vinylphenol is greater than 1. The second most important factor for determining the separation factor is a difference in solubility in water. With increasing number of carbon atoms in the side chains, the solubility in water decreases, and the separation factor with respect to vinylphenol becomes even greater. Phenol has a separation factor of less than 1 because phenol is slightly more acidic than vinylphenol and has a higher solubility in water. The separation factor of cresol with respect to vinylphenol is not so large since cresol has a higher solubility in water although cresol is less acidic than vinylphenol. Vinylphenol polymer has a separation factor of much less than 1 as in the case of strongly acidic impurities because the vinylphenol polymer alkali salt has high solubility in water although it is less acidic than vinylphenol.

Thus, vinylphenol can be easily separated by alkali extraction. Impurities having a separation factor of 1 cannot be separated, but fortunately, crude vinylphenol does not contain such impurities.

Impurities having a separation factor of at least about 1.3, preferably at least 1.5, or a separation factor of not more than about 0.77, preferably not more than 0.67 can be separated from vinylphenol on a commercial scale.

For convenience, hereinafter, the case of being smaller than a separation factor (1.0 - 1.3) of vinylphenol is referred to as "more acidic" than vinylphenol and the case of being larger than that is referred to as "less acidic" than vinylphenol. Thus, it has been confirmed that vinylphenol can be separated from phenol, other alkylphenols and vinylphenol polymer by alkali extraction.

Phenol and ethylphenol account for a majority of the impurities contained in crude vinylphenol, and they can be separated easily because of large difference of the separation factor. The vinylphenol polymer can be easily separated because it is readily extractable in the aqueous phase. Cresol has a separation factor closest to that of vinylphenol, but crude vinylphenol contains only a small amount of cresol. This small amount of cresol can be separated from vinylphenol by alkali extraction using a multi-staged extractor. However since cresol has a higher solubility in water than vinylphenol, cresol can be removed from vinylphenol by washing with water.

Various procedures are available for removing cresol by washing with water. For example, vinylphenol, cresol and impurities having stronger acidity than these can be extracted from crude vinylphenol using an alkali extracting procedure, and then the cresol together with the waste water can be removed in a reflux zone of the extracting step to be described. In this case, a quite long refluxing zone can be used and water can be fed to the upper part of the refluxing zone to increase the effect of water washing. Alternatively, the organic phase obtained from the refluxing zone of the alkali extraction step can be passed through a water-washing tower. Furthermore, in order to remove cresol by washing with water, the crude vinylphenol can be washed with water prior to the alkali extraction step by passed the crude vinylphenol through a water-washing tower. In this case, phenols such as vinylphenol and alkylphenols must not be present in the form of the alkali metal or alkaline earth metal salts in the crude vinylphenol, because these alkali metal or alkaline earth metal salts are removed on washing.

When phenol is present in the crude vinylphenol, phenol is also separated from the crude vinylphenol as a result of washing the crude vinylphenol with water to remove cresol and thus separate the cresol from vinylphenol. The ability to separate cresol and phenol from vinylphenol can be readily understood from the results in Table 2 below which show the distribution coefficients of vinylphenol, cresol and phenol between organic solvents and water and the ratios of these. Substances having distribution coefficient ratios of at least 1.5 can be effectively separated.

Table 2

| Organic Solvent | Distribution Coefficient | | | Distribution Coeffcient Ratio | |
|---|---|---|---|---|---|
| | Vinyl-phenol | Phenol | Cresol | Vinyl-phenol / Phenol | Vinyl-phenol / Cresol |
| Benzene | 37 | 5.2 | 25 | 7.1 | 1.5 |
| p-Xylene | 26 | 3.1 | 12 | 8.4 | 2.2 |
| Diethyl Ether | 400 | 67 | 200 | 6.0 | 2.0 |
| n-Butyl Ether | 200 | 19 | 84 | 11 | 2.4 |
| Nitrobenzene | 123 | 10 | 54 | 12 | 2.3 |
| Nitromethane | 63 | 12 | 35 | 5.3 | 1.8 |
| n-Hexane | 1.3 | 0.18 | 0.86 | 7.2 | 1.5 |
| Dichloroethane | 45 | 5.7 | 27 | 7.9 | 1.7 |

It has also been found that the use of a specific organic solvent can lead to the smooth and efficient performance of the extracting procedure without any dificulty due to the polymerization of vinylphenol, and that as this organic solvent, solvents which are capable of dissolving the components of the crude vinylphenol but which are insoluble or difficulty soluble in water, such as aromatic hydrocarbons, ethers, alcohols, nitro compounds, halogenated hydrocarbons, nitriles, sulfones, sulfoxides and mixtures of these, are preferred. Mixtures of these compounds and aliphatic hydrocarbons or alicyclic hydrocarbons are also suitable as the organic solvents.

It has also been found that alcoholic solvents such as alcohols and mixtures containing alcohols among these organic solvent insoluble or difficulty soluble in water have good ability to dissolve the vinylphenol polymer and since the use of these alcoholic solvents can lead to the smooth extraction of vinylphenol from crude vinylphenol containing a relatively large amount of vinylphenol polymer and does not involve any difficulty due to the vinylphenol polymer, alcoholic solvents are especially preferred organic solvents.

The various organic solvents described above also can be effectively used for separating vinylphenol from cresol, etc. by washing with water.

Accordingly, the present invention provides a process for separating and purifying vinylphenol which comprises subjecting crude vinylphenol at least once to an extracting procedure, if desired, in combination with a water washing procedure, by countercurrently contacting crude vinylphenol with an aqueous alkali solution as an extracting agent while feeding an organic solvent selected from the group consisting of the above-described solvents or containing at least one of the above-described solvents into the extracting system and refluxing the solute, thereby fractionating the crude vinylphenol into a fraction containing purified vinylphenol and a fraction containing impurities more acidic than vinylphenol and/or a fraction containing impurities less acidic than vinylphenol.

Generally, crude vinylphenol produced by the various methods described above is a mixture of vinylphenol, impurities more acidic than vinylphenol consisting mainly of phenol and carboxylic acids and impurities less acidic than vinylphenol consisting mainly of alkylphenols such as cresol, ethylphenol, propylphenol or butylphenol and also containing non-acidic substances such as hydrocarbons. Specifically, crude vinylphenol contains about 10 to 95% by weight of vinylphenol, about 0 to 50% by weight of phenol, about 0 to 90% by weight of ethylphenol, about 0 to 5% by weight of cresol, about 0 to 5% by weight of vinylphenol polymer, and about 0 to several percent by weight of other alkylphenol, carboxylic acids and hydrocarbons.

According to the process of this invention, vinylphenol of high purity can be separated from such crude vinylphenol.

The alkali which can be used as an extracting agent in the form of an aqueous solution is water-soluble alkali metal hydroxides or alkaline earth metal hydroxides. For example lithium hydroxide, sodium hydroxide, potassium hydroxide, rubidium hydroxide, magnesium hydroxide, calcium hydroxide, cesium hydroxide, strontium hydroxide, barium hydroxide, etc. The concentration of the alkali in the aqueous alkali solution is not particularly limited, but usually about 0.05 to 3 normal-solution. Preferably, continuous extraction is performed using a tower-type extractor, the appropriate concentration of the alkali is not more than about 1 normal because such a concentration facilitates the extracting procedure. Where a batchwise countercurrent extractor is used, the operation can be easily performed even if the alkali concentration is above about 1 normal, for example, about 2 normal.

Alkali in the aqueous alkali solution is required in an amount of at least chemical equivalents necessary to convert vinylphenol and/or other phenols to be extracted into the alkali salt. Actually, the amount varies greatly depending upon the content of vinylphenol and/or other phenols in crude vinylphenol, the content of vinylphenol and/or other phenols in the reflux recycled, etc. The amount of alkali is usually about 1.01 to about 100 moles, preferably about 1.3 to about 30 moles, per 1 mole of the components (vinylphenol and/or other phenols) to be extracted in the starting crude vinylphenol.

Organic solvents fed to the extracting system dissolve the individual components of the crude vinylphenol, but are insoluble or difficulty soluble in water (at the extraction temperature and pressure). Solubility of those organic solvents in water is usually below about 8g/100gH$_2$O at 20° C. Examples of the organic solvents include aromatic hydrocarbons such as benzene, toluene, xylene, ethylbenzene or tetralin; ethers having 4 or more carbon atoms such as diethyl ether, dipropyl ether, di-sec.-butyl ether, di-benzyl ether, benzyl ethyl ether or courmarone; alcohols having 5 or more carbon atoms such as amyl alcohol, hexanol heptanol, cyclohexanol or benzyl alcohol; nitro compounds such as nitromethane, nitropropane, nitrobenzene or o-nitrotoluene; halogenated hydrocarbons such as chlorobenzene, bromobenzene, (o, m, p—) chlorotoluene, chloronaphthalene, tetrachloroethane, trichloropropane, or trichlorotrifluoroethane; nitriles such as benzonitrile, tolunitrile, 2,4-dimethylbenzonitrile, 4-isopropyl benzonitrile, butyronitrile or capronitrile; sulfoxides such as dibutyl sulfoxide or methyl phenyl sulfoxide; sulfones such as ethyl tolyl sulfone, butylolyl sulfone, dibutyl sulfone or ethyl isobutyl sulfone, and mixtures of these solvents.

Mixtures of aliphatic hydrocarbons such as n-hexane, n-pentane or iso-octane or halohydrocarbons such as carbon tetrachloride, dichloromethane, trichloroethylene or isobutyl chloride with the above aromatic hydrocarbons, ethers, alcohols, nitro compounds, halogenated hydrocarbons, nitriles, sulfoxides, or sulfones can also be used in the invention as the organic solvents fed into the extraction system.

Differences in the type of the organic solvents used affect the purification of crude vinylphenol to some extent, but not to any serious extent. This can be readily understood from the data in Table 3 below which show the separation factor of p-ethylphenol from p-vinylphenol measured with respect to various solutions of p-vinylphenol and p-ethylphenol in different types of organic solvents maintained at 5° C. The data in Table 3 clearly indicate that the separation factor does not change with the types of organic solvent to an extent such that separation becomes impossible.

Table 3

Separation Factor of p-Ethylphenol with respect to p-Vinylphenol

| Organic Solvent | Separation Factor |
| --- | --- |
| Benzene | 6.2 |
| Xylene | 5.9 |
| n-Octanol | 3.4 |
| Di-sec.-Butyl Ether | 4.6 |
| Nitrobenzene | 3.8 |
| n-Hexane | 8.5 |
| Chlorobenzene | 6.7 |
| Carbon Tetrachloride | 7.3 |
| Benzonitrile | 4.2 |
| n-Butyl o-Tolyl Sulfone | 4.0 |

Table 3-continued

| Separation Factor of p-Ethylphenol with respect to p-Vinylphenol | |
|---|---|
| Organic Solvent | Separation Factor |
| Methyl Phenyl Sulfoxide | 3.8 |

The amount of these organic solvents used varies greatly depending upon the kind of organic solvents, the vinylphenol content in the crude vinylphenol, the purity of final vinylphenol, etc., but is usually about 1 to about 100 times by weight, preferably about 2 to about 50 times by weight, based on the weight of the starting crude vinylphenol.

Where crude vinylphenol containing a relatively large amount of vinylphenol polymers is used as a starting material, it is preferred to use alcoholic solvents. Solvents other than alcoholic solvents are poor in an ability dissolving vinylphenol polymer, so that the use of those other solvents tends to gradually precipitate scale (mainly comprising partial alkali salt of vinylphenol polymer, i.e., a compound in which a part of all phenolic OH groups contained in the polymer converts into alkali salt) on the inner wall of extractor and pipes, the stirrer and the like, as compared with the use of the alcoholic solvents. As a result, due to the hindrances such as blocking of pipes, stickness of rotating portions, etc., it is difficult to conduct a stable and continuous extraction operation for a long period of time. In order to overcome this disadvantage, it is desirable to use as much as possible the above-mentioned alcoholic solvents as organic solvents, and further the extraction operation may be conducted in the presence of the organic solvents (containing alcohols) together with the water-soluble alcohols. Examples of the water-soluble alcohols include lower alcohols having 1 to 4 carbon atoms, such as methanol, ethanol, propanols, butanols, ethylene glycol, diethylene glycol, glycerine or the like. Of these alcohols, methanol and/or ethanol are/is preferred. It is assumed that the ability that these water-soluble alcohols dissolve the scale to transfer it into the aqueous alkali solution is good. The amount of water-soluble alcohols used is finally determined by the polymer content in the crude vinylphenol, but is generally about 0.5 to about 50% by weight, preferably about 1 to 20% by weight, based on the weight of aqueous alkali solution used. If the amount of water-soluble alcohols is too large, the purity and yield of vinylphenol lower, and if the amount thereof is too small, a sufficient scale preventing effect cannot be achieved. These water-soluble alcohols may be introduced from any portion of an extractor if it is for the purpose of introducing in an extracting system and the entire amount used may be introduced from one portion or may be introduced dividedly from at least two portions. Further, the alcohols may be introduced into the extracting system continuously or intermittently. It is generally advantageous from the viewpoint of handling that the water-soluble alcohols are divided into two solutions, and one is used together with the crude vinylphenol and another is used together with the aqueous alkali solution.

The process of this invention can be performed by liquid-liquid countercurrent extraction, and an extractor having a reflux zone is preferably used. The basic extracting procedure will be described below by reference to an example of using a tower-type extraction device.

Generally, crude vinylphenol is dissolved in the organic solvent described above, and then fed to an intermediate stage of an extraction tower. Where the starting crude vinylphenol is liquid at the extracting temperature, it is not always necessary to dissolve the crude vinylphenol in the organic solvent prior to feeding into the extraction tower, and the crude vinylphenol and the organic solvent can be separately fed into the extraction tower. The starting crude vinylphenol can also be fed into the extraction tower as an aqueous solution of its alkali metal or alkaline earth metal salt or in the form which partly contains the alkali metal or alkaline earth metal salt, hereinafter simply alkali salt.

An aqueous alkali solution is fed into the upper part of the extraction tower. In a contacting zone of the extraction tower, the crude vinylphenol is contacted coutercurrently with the aqueous alkali solution. The raffinate is obtained from the top of the extraction tower, and an aqueous solution containing an alkali salt of vinylphenol and/or alkali salts of impurities more acidic than vinylphenol is obtained as an extract from the bottom of the extraction tower. The extract is introduced into a reflux zone, and an acid and an organic solvent described above are further fed into the reflux zone. In the reflux zone, the extract is decomposed with the acid to free a solute composed of the vinylphenol and/or the impurities more acidic than vinylphenol, and the free solute is dissolved in the organis solvent. The aqueous phase in the reflux zone is withdrawn from the reflux zone, and the organic phase composed of the organic solvent and the free solute in the reflux zone is partly refluxed to the bottom of the extraction tower in order to increase the efficiency of purification and separation. The remainder of the organic phase is withdrawn from the reflux zone. Examples of suitable acids fed into the reflux zone to decompose the extract are acids such as carbonic acid, $CO_2$ gas, sulfurous acid, $SO_2$ gas, sulfuric acid, hydrochloric acid, HCl gas, nitric acid or phosphoric acid, and acidic salts of these acids such as sodium bicarbonate, potassium bicarbonate, etc. Acids are used in an amount sufficient for neutralizing alkali salts of vinylphenol and other impurities contained in the extract.

Since vinylphenol is very susceptible to polymerization, the above extracting procedure should be carried out at a relatively low temperature, usually about $-10°$ to $+40°$ C., preferably $0°$ to $30°$ C. This procedure is also carried out at atmospheric, reduced or atmospheric pressure.

Usually, the above-described extracting procedure is performed in two-step wise in order to separate purified vinylphenol from the impurities more acidic than vinylphenol and the impurities less acidic than vinylphenol. An example of this procedure is as follows* First, in a first extraction step, the extraction procedure is performed using an aqueous alkali solution in an amount which leads to the substantial extraction of only the impurities more acidic than vinylphenol, whereby only the impurities more acidic than vinylphenol are substantially extracted from the crude vinylphenol. In this operation, the extract is an aqueous solution containing the alkali salts of the impurities more acidic than vinylphenol, and the organic phase withdrawn from the reflux zone contains the impurities more acidic than vinylphenol. These impurities comprise mainly phenol. On the other hand, the raffinate contains vinylphenol and impurities less acidic than vinylphenol. The raffinate formed in the first extraction step is used as an extraction feed for a second extraction step.

The second extraction step is carried out using an aqueous alkali solution in an amount which leads to the substantial extraction of only vinylphenol, and only vinylphenol is selectively extracted from the raffinate of the first extraction step. The extract formed is an aqueous solution containing the alkali salt of vinylphenol, and the organic phase withdrawn from the reflux zone contains purified vinylphenol. The raffinate in the second extraction step contains mainly impurities less acidic than vinylphenol.

The extraction procedure can aslo be performed in the following manner in order to separate vinylphenol of high purity from crude vinylphenol.

In the first extraction step, extraction is performed using an aqueous alkali solution in an amount which leads to the substantial extraction of vinylphenol and impurities more acidic than vinylphenol, whereby the vinylphenol and the impurities more acidic than vinylphenol are substantially extracted from crude vinylphenol. The raffinate formed contains impurities less acidic than vinyl phenol, and the organic phase obtained from the reflux zone contains vinylphenol and impurities more acidic than vinylphenol. Then, this organic phase is extracted in the second extraction step with an aqueous alkali solution in an amount which leads to the substantial extraction of the impurities more acidic than vinylphenol, whereby only the impurities more acidic than vinylphenol are substantially extracted. The raffinate contains the purified vinylphenol.

In this latter extraction procedure example, the extract in the contacting zone of the first extracting step, which is an aqueous solution containing an alkali salt of vinylphenol and alkali salts of impurities more acidic than the vinylphenol, can be directly fed into the second extraction step. In this case, only vinylphenol and impurties more acidic than the vinylphenol are freed by the acid treatment in the reflux zone of the first extraction step in amounts required for refluxing to the contacting zone of this step. On the other hand, the organic phase in the reflux zone is refluxed to the contacting zone of the first extracting step in its entirety.

In separating vinylphenol from crude vinylphenol, a procedure of water washing can be used in combination with the alkali extracting procedure as will be described below.

According to this procedure, the crude vinylphenol is first washed with water to remove impurities more soluble in water than the vinylphenol, such as cresol and phenol, and then, the remaining crude vinylphenol is subjected to the alkali extraction procedure. Impurities more acidic than vinylphenol which are contained in crude vinylphenol sometimes consist only of easily water-soluble substances such as phenol and cresol. In such a case, it is sufficient for the alkali extracting procedure to be carried out only once. In this alkali extracting step, the extraction is carried out using an aqueous alkali solution in an amount sufficient to extract substantially only vinylphenol. The raffinate resulting from this alkali extracting step contains impurities less acidic than vinylphenol, and the extract contains vinylphenol. Washing of the crude vinylphenol with water can be carried out by conventional means employed for washing liquid organic substances with water. For example, this washing can be performed using a tower-type water-washing device in the following manner. Crude vinylphenol to be washed with water and water are fed into the water-washing tower so that they are countercurrently contacted with each other. If desired, an organic solvent is fed into the bottom part of the water-washing tower. The water-washed organic phase is withdrawn from the top of the water-washing tower, and waste water containing substances more soluble in water than vinylphenol, such as cresol and phenol, is withdrawn from the bottom of the water-washing tower. The organic solvent fed into the water-washing tower is preferably the same type of organic solvent which is suitable for use in the alkali extraction step described above. The vinylphenol in the crude vinylphenol fed into the water washing step should not be in the form of an alkali salt because the alkali salt of vinylphenol would be lost by water washing. The water procedure is carried out at a relative low temperature, usually about 0° – 40° C. preferably 0° – 30° C under atmospheric, reduced or super pressure.

In the above process comprising the combination of the alkali extraction procedure and the water washing procedure, the sequence of the alkali extraction and the water washing can be reversed. For example, the crude vinylphenol is subjected to the alkali extraction procedure to fractionate the crude vinylphenol into a fraction containing vinylphenol and impurities more acidic than the vinylphenol, such as cresol and phenol, and another fraction containing inpurities less acidic than the vinylphenol, and then the first-mentioned fraction is washed with water to obtain purified vinylphenol.

Water-washing of the fraction containing vinylphenol and substances more soluble in water than the vinylphenol, such as cresol, to remove these more soluble substances can be performed in a water washing step provided separately after the alkali extraction step, or can be effected in the reflux zone of the alkali extraction step after sufficient amounts of water have been fed to the reflux zone. In the latter case, the impurities more soluble in water than vinylphenol are removed together with the waste water of the reflux zone. According to the latter method, if the impurities more acidic than vinylphenol which are contained in crude vinylphenol are substances more soluble in water than the vinylphenol, such as phenol and cresol, purified vinylphenol can be obtained from the reflux zone of the above alkali extraction step by subjecting the crude vinylphenol to only one alkali extraction.

In addition, in the process comprising the two alkali extraction steps described above, it is not always necessary to fractionate vinylphenol from cresol which has an acidity close to that of the vinylphenol, using the alkali extraction. Instead, the alkali extraction can be performed so that vinylpenol and cresol are contained in the same fraction, and then the vinylphenol is separated from the cresol by washing with water.

The process of this invention can also be applied to the purification of crude vinylphenol which does not substantially contain impurties that are more acidic or less acidic than the vinylphenol. The purification of such crude vinylphenol does not require a two-step extraction procedure, and one extraction step is sufficient.

One specific embodiment of the process of this invention will be described in greater details, by reference to FIG. 1 which is a flowsheet showing a tower-type continuous extraction in accordance with the present invention.

Crude vinylphenol containing vinylphenol and impurities more acidic and less acidic than vinylphenol, either as such or as a solution in an organic solvent, is fed through a line 1 into an intermediate stage of a first extraction tower 2. An aqueous alkali solution in an amount sufficient for extraction of only vinylphenol and impurities more acidic than vinylphenol from the crude vinylphenol is fed through a line 3 into the upper of the first extraction tower 2. The crude vinylphenol is contacted countercurrently with the aqueous alkali solution, and through a line 4, a raffinate containing impurities less acidic than vinylphenol is discharged from the top of the first extraction tower 2. An aqueous solution containing the alkali salts of impurities more acidic than vinylphenol and of vinylphenol is discharged from the bottom of the first extraction tower 2 through a line 5 and fed into the upper part of a reflux zone 6. An acid is further fed into the upper portion of the reflux zone 6 through a line 7, and an organic solvent is fed into the bottom of the reflux zone through a line 8. The reflux zone is constructed in the same manner as the extraction tower, and vinylphenol and impurities more acidic than the vinylphenol are freed in the reflux zone by the action of the acid and then extracted with the organic solvent. Waste water is discharged from the bottom of the reflux zone 6 through a line 9, and an organic phase containing vinylphenol and impurities more acidic than the vinylphenol is withdrawn from the top of the reflux zone 6 through a line 10. A part of the organic phase is refluxed to the bottom of the first extraction tower 2 through a line 11, and the remaining part is fed into an intermediate stage of a second extraction tower 13 through a line 12. An aqueous alkali solution in an amount sufficient for extraction of only the impurities more acidic than the vinylphenol is fed into the upper part of the second extraction tower 13 through a line 14, and the organic phase is contacted countercurrently with the aqueous alkali solution. A raffinate containing vinylphenol is withdrawn from the top of the second extraction tower 13 through a line 15, and an aqueous solution containing the alkali salts of the impurities more acidic than vinylphenol is withdrawn from the bottom of the second extraction tower 13 through a line 16 and fed into the upper part of a reflux zone 17. The reflux zone 17 has the same function as the reflux zone 6. An acid and an organic solvent are fed into the reflux zone 17 through lines 18 and 19. Waste water is fed through a line 20 and an organic phase containing impurities more acidic than vinylphenol is fed through a line 21. A part of the organic phase withdrawn is refluxed to the bottom of the second extraction tower 13 through a line 22, and the remainign part is withdrawn through a line 23. As a result of this procedure, vinylphenol of high purity is obtained as a raffinate of the second extraction tower 13.

In FIG. 1, the extraction towers are separated from the reflux zones but alternatively, the reflux zone can be incorporated with the extraction tower at the bottom of the extraction tower.

The system described by the flowsheet shown in FIG. 2 is one modification of the system described by the flowsheet shown in FIG. 1, and is the same as the system shown in FIG. 1 except as noted below. In the system of FIG. 2, the aqueous solutiong containing an alkali salt of vinylphenol and alkali salts of impurities more acidic than the vinylphenol as withdrawn through line 5 from the bottom of the first extraction tower 2 is fed into the reflux zone 6 in an amount required to reflux the solute to the first extraction tower 2, and the remainder of the aqueous solution is fed into the second extraction tower through line 12. The organic phase in the reflux zone 6 is refluxed in its entirety to the first extraction tower 2 through lines 10 and 11.

FIG. 3 is a flowsheet showing another embodiment of the present invention. The system shown in FIG. 3 is also the same as that shown in FIG. 1 except as noted below. An aqueous alkali solution is fed into the first extraction tower 2 through line 3 in an amount sufficient for extracting only those impurities which are more acidic than vinylphenol. And a raffinate containing vinylphenol and impurities less acidic than the vinylphenol is withdrawn from the top of the first extraction tower 2 through the line 4. The raffinate is then fed into the second extraction tower as a material to be extracted. An aqueous solution containing the alkali salts of impurities more acidic than the vinylphenol is withdrawn from the bottom of the first extraction tower 2 through line 5, and then fed into the reflux zone 6. The organic phase withdrawn from the reflux zone 6 through line 10 is partly refluxed to the first extraction tower 2 through line 11, and the remainder is withdrawn from the system. The raffinate withdrawn from the first extraction tower 2 through line 4 is fed into the second extraction tower 13, and an aqueous alkali solution is also fed into the second extraction tower 13 through line 14 in an amount required to extract only vinylphenol. In the second extraction tower 13, a raffinate containing impurities less acidic than vinylphenol is withdrawn through line 15, and an aqueous solution containing an alkali salt of vinylphenol is withdrawn through line 16. The aqueous solution is then fed into the reflux zone 17. The organic phase withdrawn from the reflux zone 17 through line 21 is a fraction containing purified vinylphenol.

Figure 5:
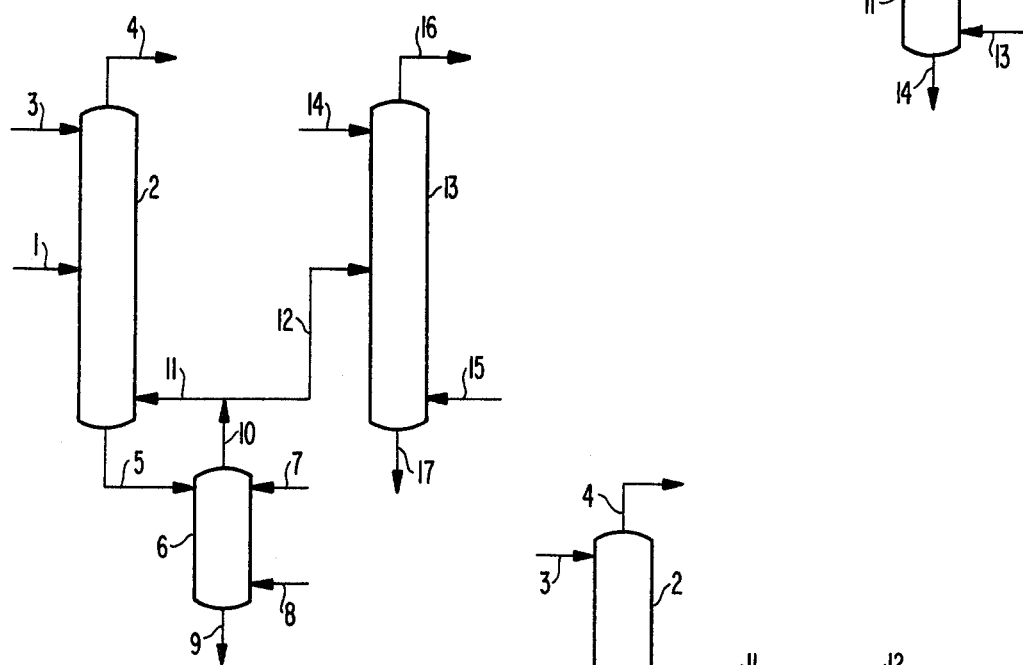
Figure 6:
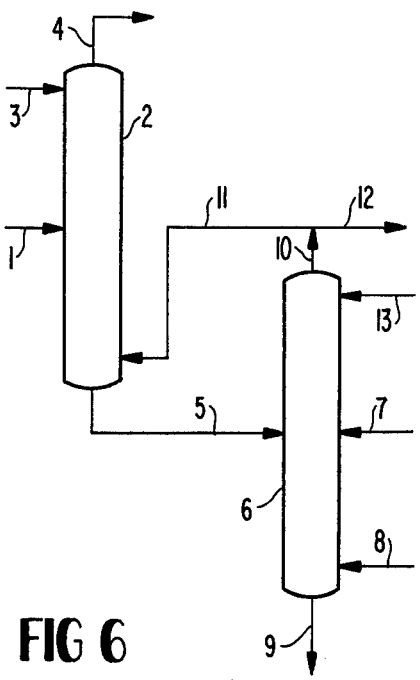

FIGS. 4, 5 and 6 are flowsheets showing other embodiments of the present invention, which relate to a process comprising an alkali extraction procedure and a water washing step. The system shown in these figures are suitable for purifying the crude vinylphenol in which impurities more acidic than the vinylphenol are substances more soluble in water than the vinylphenol, such as phenol and cresol.

The system shown in FIG. 4 comprises the replacement of the first extraction tower 2 and the reflux zone 7 shown in FIG. 3 by water washing towers. According to the system shown in FIG. 4, crude vinylphenol is fed into an intermediate stage of a water washing tower 2 through a line 1; water is fed into the upper part of the water washing tower 2 through line 3; and an organic solvent is fed into the bottom of the water washing tower 2 through line 4. Waste water containing phenol and cresol, etc. is discharged from the bottom of the water washing tower 2 through line 5. An organic phase containing crude vinylphenol from which phenol and cresol hav been removed is withdrawn from the top of the water washing tower 2 through line 6. The organic phase is then fed into an intermediate stage of an extraction tower 7. An aqueous alkali solution is further fed into the upper part of the extraction tower 7 through line 8 in an amount required to extract vinylphenol. A raffinate containing impurities less acidic than vinylphenol is withdrawn from the top of the extraction tower 7 through line 9, and an aqueous solution containing an alkali salt of vinylphenol is withdrawn from the bottom of the extraction tower 7 through line 10. the aqueous solution is then fed to the upper part of a reflux zone 11. Furthermore, an acid is fed into the upper part of the reflux section 11 through the line 12, and an organic solvent, into the lower part of the reflux zone through line 13. Waste water is withdrawn from the bottom of the relfux zone 11 through line 14, and an organic phase containing purified vinylphenol is withdrawn from the top of the reflux zone 11 through line 15. A part of this organic phase is refluxed to the bottom of the extraction tower through line 16, and the remainder is withdrawn through line 17.

The system shown in FIG. 5 comprises the replacement of the second extraction tower 13 and the reflux zone 17 of the system shown in FIG. 1 by water washing towers. In FIG. 5, the reference numerals 2, 6 and 13 respectively represent an extraction tower, a reflux zone, and a water washing tower. The system up to the point where a part of the organic phase withdrawn from the reflux zone 6 through line 10 is fed into the water washing tower 13 is quite the same as the system using the first extraction tower 2 and the accompanying reflux zone 6 in FIG. 1. In the system shown in FIG. 5, a part of the organic phase withdrawn from the reflux zone 6 through line 10 is fed into an intermediate stage of the water washing tower through line 12. Furthermore, water is fed into the upper part of the water washing tower through line 14, and an organic solvent is fed into the lower part of the water washing tower through line 15. An organic phase containing purified vinylphenol is withdrawn from the top of the water-washing tower through line 16, and waste water containing phenol and cresol is discharged from the bottom of the water washing tower through line 17.

In the system shown in FIG. 6, crude vinylphenol is fed into an intermediate stage of an extraction tower 2 through line 1, and an aqueous alkali solution is fed into the upper part of the extraction tower 2 through line 3 in an amount required to extract vinylphenol and impurities more acidic than vinylphenol, such as phenol and cresol. The solute is refluxed through the line 11, to the lower part of the extraction tower 2. On the other hand, a raffinate containing impurities less acidic than vinylphenol is withdrawn from the top of the extraction tower 2 through line 4, and from the bottom of the extraction tower 2, an aqueous solution containing alkali salts of vinylphenol and impurities more acidic than vinylphenol, such as phenol and cresol, is withdrawn through line 5. The above system is the same as that of the first extraction tower shown in FIG. 1. The aqueous solution withdrawn through line 5 is fed into an intermediate stage of the reflux zone 6. Furthermore, an acid is fed into an intermediate stage of the reflux zone 6 through line 7, an organic solvent into the lower part of the reflux zone 6 through line 8, and water into the upper part of the reflux zone 6 through line 13. On the other hand, waste water containing impurities such as phenol and cresol is withdrawn from the bottom of the reflux zone 6 through line 9, and from the top of the reflux zone 6, an organic phase containing purified vinylphenol is withdrawn through line 10. A part of the organic phase is refluxed to the lower part of the extraction tower 2 through line 11, and the remainder is withdrawn through line 12.

Figure 7:
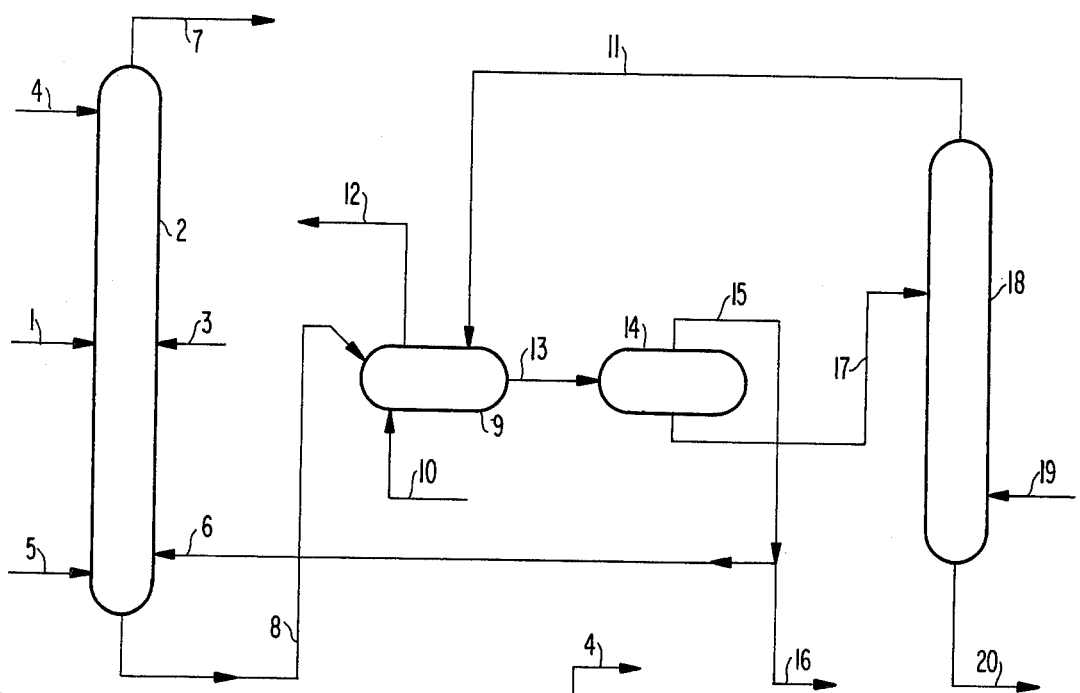

FIG. 7 is a flowsheet showing another embodiment of the present invention. Crude vinylphenol (containing no phenol) is fed together with methanol through line 1 and an organic solvent is fed through line 3 into an intermediate stage of an extraction tower 2 separately. Aqueous alkali solution in an amount sufficient for extracting vinylphenol only is fed together with methanol into an upper part of the extraction tower through line 4. Further, a part of aqueous alkali solution is fed into a lower part of extraction tower through line 5, and an organic phase containing vinylphenol and the organic solvent is recycled as a reflux fraction to the lower portion of the extraction tower through line 6. In addition, aqueous alkali solution fed from line 5 is used specifically to prevent the formation of scale on an inner wall of line 8. This is to dissolve in aqueous alkali solution as partial alkali salt of polymer again since the partial alkali salt of vinylphenol polymer which is formed in extraction tower 2 and is dissolved in aqueous alkali solution reacts with a large amount of vinylphenol (acidic material) contained in the reflux fraction fed from line 6 to neutralize thereby being apt to precipitate. It is more preferred in preventing the scale formation to introduce aqueous alkali solution together with water-soluble alcohols such as methanol. A raffinate containing impurities less acidic than vinylphenol, hydrocarbons and organic solvents is withdrawn from the top of the extraction tower through line 7. An aqueous solution (extract) containing alkali salt of vinylphenol is withdrawn from the bottom of extraction tower through line 8 and is introduced into a reflux zone 9. Acid is introduced through line 10 and organic solvent is introduced through line 11 into the reflux zone 9. In the reflux zone, alkali salt of vinylphenol and partial alkali salt of polymer are neutralized with an acid and freed, and simultaneously only vinylphenol dissolves in the organic solvent again. The freed polymer is difficult to dissolve in organic solvents such as toluene, and, as a result, is crystallized and withdrawn out of the system through line 12. A mixture containing vinylphenol from which polymer is removed, organic solvents and water is introduced into a separator 14 through line 13 and is separated into an organic solvent containing vinylphenol and an aqueous solution. The organic solvent is withdrawn through line 15, and a part thereof is recycled as a reflux fraction to the lower part of the extraction tower 2 and the remainder is withdrawn through line 16 as an organic solvent containing pure vinylphenol. On the other hand, the aqueous solution from the separator 14 is introduced into a recovery tower 18 through line 17. In the recovery tower 18, the organic solvent introduced from line 19 contacts with an aqueous solution to extract and recover a small amount of vinylphenol contained in the aqueous solution. The organic solvent containing a small amount of vinylphenol is recycled to the reflux zone 9 from the top of the recovery tower through line 11. Further, a waste water is withdrawn from the bottom of the recovery tower through line 20.

Figure 8:
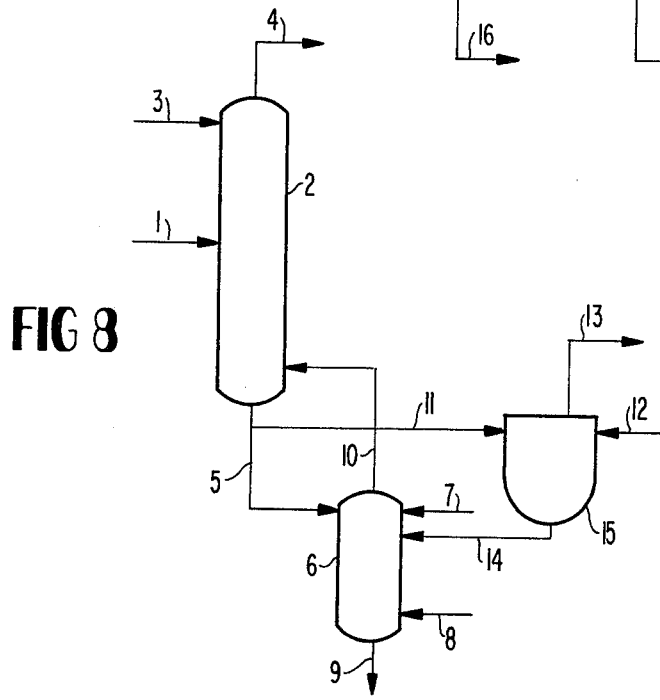

FIG. 8 is a flowsheet showing still another embodiment of the present invention. The system shown in FIG. 8 is convenient when the desired vinylphenol is p-vinylphenol having a high melting point, and it is not necessary to separate impurities more acidic than vinylphenol. In FIG. 8, crude vinylphenol is fed into an intermediate stage of extraction tower 2 through line 1, and an aqueous alkali solution necessary for extracting vinylphenol and impurities more acidic than vinylphenol is fed into the upper part of the extraction tower 2 through line 3. A raffinate containing impurities less acidic than vinylphenol is withdrawn from the top of the extraction tower 2 through line 4, and an aqueous solution containing alkali salts of vinylphenol and impurities more acidic than vinylphenol is withdrawn from the bottom of the extraction tower 2 through line 5. The aqueous solution so withdrawn through line 5 is fed only in an amount necessary for refluxing the vinylphenol and the impurities more acidic than vinylphenol to the upper part of the reflux zone 6. An organic solvent is fed into the lower part of the reflux zone 6 through line 8, and an acid is fed into the upper part of the reflux zone 6 through line 7. An organic phase containing vinylphenol and impurities more acidic than vinylphenol is withdrawn from the top of the reflux zone 6 through line 10, and all of the organic phase is refluxed to the lower part of the extraction tower 2. The remainder of the aqueous solution withdrawn from the bottom of the extraction tower 2 through line 5 is fed into a crystallization tank 15 through line 11, and the crystallization tank 15 is further charged with an acid through line 12. In the crystallization tank 15, vinylphenol is freed by the action of the acid fed, and the freed vinylphenol is crystallized by being maintained at a temperature below its melting point. The crystals of vinylphenol are removed from an upper section 13 of the crystallization tank, and the crystallization mother liquor is withdrawn from the lower part of the crystallization tank 15 through line 14. The crystallization mother liquor so withdrawn through line 14 is fed into the upper part of the reflux zone 6 in order to recover the vinylphenol remaining in the mother liquor.

This system comprises an example in which vinylphenol is recovered by a crystallization procedure from an aqueous solution containing an alkali salt of vinylphenol obtained by an alkali extraction procedure. This embodiment is also within the scope of the present invention.

Figure 9:
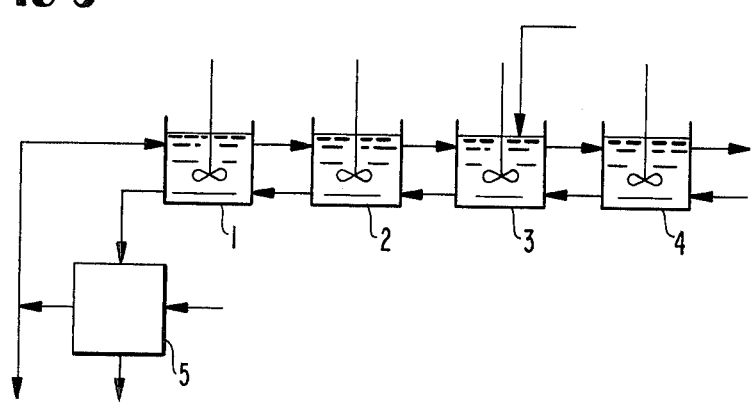

FIG. 9 is a flowsheet of a batchwise countercurrent extraction which is another embodiment of the present invention. In FIG. 9, the reference numeral 1 represents a first extraction tank equipped with a stirrer, 2 a second extraction tank equipped with a stirrer, 3 a third extraction tank equipped with a stirrer, 4 a fourth extraction tank equipped with a stirrer, and 5 a reflux zone. The arrows designated at 1 to 5 show the destination of transferring liquid or the feeding or discharging of liquid.

In the steady state in this system, an aqueous alkali solution and an organic solvent containing at least one of the components of crude vinylphenol are placed in each of the extraction tanks, stirred, and allowed to stand to effect extraction. After completion of the extracting procedure, the aqueous phase in the first extraction tank 1 is transferred to the reflux zone 5, the aqueous phase in the second extraction tank 2 is transferred to the first extraction tank 1, the aqueous phase in the third extraction tank 3 is transferred to the second extraction tank 2, and the aqueous phase in the fourth extraction tank 4 is transferred to the third extraction tank 3. A fresh aqueous alkali solution is added to the fourth extraction tak 4. In this state, the extraction procedure is repeated. The organic phase in the fourth extraction tank 4 is withdrawn from the extraction system, and the organic phase in the third extraction tank 3 is transferred to the fourth extraction tank 4. The organic phase in the second extraction tank 2 is transferred to the third extraction tank 3, and the organic phase in the first extraction tank 1 is transferred to the second extraction tank 2. A part of the organic phase obtained in the reflux zone 5 is fed into the first extraction tank 1, and the starting crude vinylphenol is placed in the third extraction tank 3. In addition to the aqueous phase from the first extraction tank 1, an acid and an organic solvent are fed into the reflux zone 5 where the alkali salts of the components of crude vinylphenol are decomposed with the acid and the components of crude vinylphenol which have been thus freed are extracted with the organic solvent. A part of the organic phase formed in the reflux zone 5 is refluxed to the first extraction tank 1, and the remaining part is withdrawn from the extraction system. The aqueous phase in the reflux zone 5 is also withdrawn out of the system. This system is suitable for the purification of crude vinylphenol which does not sustantially contain impurities more acidic than vinylphenol or crude vinylphenol which does not substantially contain impurities less acidic than vinylphenol. When the former crude vinylphenol is used as a raw material, the organic phase withdrawn from the fourth extraction tank 4 contains the impurities less acidic than vinylphenol, and the organic phase withdrawn from the reflux zone 5 contains vinylphenol. If the latter crude vinylphenol is used as a raw material, the organic phase withdrawn from the fourth extraction tank 4 contains vinylphenol, and the organic phase withdrawn from the reflux zone 5 contains the impurities more acidic than vinylphenol.

The process of this invention makes it possible to separate highly purified vinylphenol smoothly in good yields from crude vinylphenol for a long period without involving any defficulty ascribable to the polymerization of vinylphenol during the pruifying operation nor any defficulty ascribable to vinylphenol polymer contained in the starting crude vinylphenol. The process can be performed on an industrial scale, and has enabled vinylphenol having excellent characteristics to be utilized industrially.

The following Examples are given to illustrate the process of this invention in even greater detail.

EXAMPLE 1

The separation and purification of vinylphenol were performed in accordance with the system shown in FIG. 9.

A solution in one liter of toluene of a mixture of 0.15 mol o-vinylphenol, 0.1 mol m-vinylphenol, 0.15 mol p-vinylphenol, 0.06 mol o-ethylphenol, 0.024 mol m-ethylphenol and 0.516 mol p-ethylphenol and one liter of 0.5N aqueous hydroxide solution were fed into each of 5-liter first to fourth extraction tanks each of which was equipped with a stirrer.

To effect a total reflux, the following procedure was performed as one unit. The four extraction tanks were stirred, and then allowed to stand. The aqueous phase in the first extraction tank was transferred to the reflux zone, the aqueous phase in the second extraction tank was transferred to the first extraction tank, the aqueous phase in the third extraction tank was transferred to the second extraction tank, and the aqueous phase in the fourth extraction tank to the third extraction tank. One liter of 0.5N aqueous sodium hydroxide solution was placed in the fourth extraction tank. The extraction tanks were further stirred and allowed to stand in this state. Then, the organic phase in the fourth extraction tank was discarded. The organic phase in the third extraction tank was transferred to the fourth extraction tank, the organic phase in the second extraction tank to the third extraction tank, and the organic phase in the first extraction tank to the second extraction tank. To the reflux zone, 0.75 mol of sodium bicarbonate as acids and one liter of toluene were added, whereby phenols were freed from the sodium salts of the phenols and extracted with toluene. All of the organic phase in the reflux zone was transferred to the first extraction tank and the aqueous phase was discarded. The above unit operation was repeated six times.

In each unit of the operation, ⅔ of the organic phase obtained in the reflux zone was refluxed to the first extraction tank, and the remaining ⅓ of the organic phase was withdrawn from the system and collected. A solution in 333 ml. of toluene of 0.417 mol of a mixture of vinylphenol and ethylphenol having the above composition was placed in the third extraction tank. This unit operation was performed 10 times in the steady state. In each unit operation, the organic phase withdrawn from the reflux zone was collected as an extract, and the organic phase withdrawn from the fourth extraction tank was collected as a raffinate.

As a result, 3.5 liters of a toluene solution containing 1.5 mols of a vinylphenol mixture of 37.0 mol% o-vinylphenol, 24.7 mol% m-vinylphenol, 36.9 mol% p-vinylphenol and 1.4 mol% ethylphenol was obtained as the extract. As the raffinate, 10.4 liters of a toluene solution containing 2.6 mols of an ethylphenol mixture of 9.9 mol% o-ethylphenol, 4.0 mol% m-ethylphenol, 85.1 mol% p-ethylphenol and 1.0 mol% vinylphenol was obtained.

All of the foregoing operations were carried out at a temperature between 0° C to 5° C. under atmospheric pressure.

EXAMPLE 2

The separation and purification of vinylphenol were performed in accordance with the system shown in FIG. 1.

A toluene solution containing 20% by weight of a mixture of 41.1 mol% p-vinylphenol, 53.5 mol% p-ethylphenol, 1.95 mol% phenol and 3.45 mol% p-tert.-butylphenol was fed continuously into the central portion of the first extraction tower so that the rate of feeding all phenols was 0.099 mol/hr. This extraction tower was of a rotary stirring type with an inner diameter of 22 mm and a length of 1.8 m. A 0.512 N aqueous sodium hydroxide solution was fed to a point 10 cm below the top of the first extraction tower at a rate of 240 ml./hr. The levels of both solutions were maintained at a height of 10 cm from the bottom of the tower. From the bottom of the first extraction tower, the aqueous phase was continuously withdrawn, and fed to the reflux zone at a point 10 cm below the top of the reflux zone. This reflux zone was of the same construction as the first extraction tower and had a length of 40 cm. In order to free the phenols, a 0.76N aqueous solution of sodium bicarbonate was fed into the reflux zone at a point 10 cm below the top of the reflux zone at a rate of 240 ml./hr. Furthermore, toluene was fed into the lower part of the reflux zone at a rate of 210 ml./hr. and the levels of both solutions were maintained at 10 cm below the top of the reflux zone. The aqueous phase was continuously withdrawn from the bottom of the reflux section, and the organic phase was continuously withdrawn from its upper part. The organic phase withdrawn was then fed as a total reflux into the first extraction tower at a point 10 cm above the bottom of the tower. The above total reflux operation was performed for 4 hours, and then the extraction procedure was carried out for an additional 15 hours while maintaining the reflux ratio at 1.92. During this time, 1.15 liters of a toluene solution containing 0.633 mol of a mixture of 95.3 mol% p-vinylphenol, 0.37 mol% p-ethylphenol, 4.32 mol% phenol and 0.01 mol% p-tert.-butylphenol was obtained as an extract withdrawn from the reflux zone.

This toluene solution was fed into the second extraction tower at a point ¾ from the top of the tower so that the rate of feed of all phenols was 0.0422 mol./hr., and otherwise, the total reflux operation was performed in the same way as in the case of the first extraction tower described above. The second extraction tower and a reflux zone attached to the tower had quite the same structure as the first extraction tower and the reflux zone atached thereto. After completion of the total reflux operation, the extracting operation was carried out for 5 hours while maintaining the reflux ratio at 52.4. As a result, 1.06 liters of a toluene solution containing 0.199 mol of purified p-vinylphenol of 99.4 mol% p-vinylphenol, 0.39 mol% p-ethylphenol, 0.20 mol% phenol and 0.01 mol% p-tert.-butylphenol was obtained from the top of the second extraction tower.

All of the above operations were carried out at 5° C. under atmospheric pressure.

EXAMPLE 3

The procedure of Example 2 was repeated except that a disec.-butylether solution containing 20% by weight of a mixture of 41.1 mol% of m-vinylphenol, 53.3 mol% of the m-ethylphenol, 1.95 mol% of phenol and 3.45 mol% of p-tert.-butylphenol was used as the starting material, di-sec.-butyl ether was used as the solvent fed into the reflux zone; an extraction tower having an inside diameter of 22 mm and a length of 2.2 m was used, a 0.512 N aqueous solution of sodium hydroxide was fed at a rate of 260 ml./hour; and that the total reflux ratio after the total reflux operation was adjusted to 2.1. Purified m-vinylphenol of the same purity as in Example 2 was obtained.

EXAMPLE 4

The same procedure as in the operation of the first extraction tower and the reflux zone attached thereto in Example 2 was repeated except that a toluene solution containing 20% by wieght of a mixture of 41.1 mol% p-vinylphenol, 54.9 mol% p-ethylphenol, 1.95 mol% phenol and 2.05 mol% p-cresol was used as the starting material, and the amount of sodium bicarbonate added to the reflux section was reduced by 7%.

As a result, 1.15 liters of a toluene solution containing 0.59 mol of a mixture of 96.84 mol% p-vinylphenol, 0.36 mol% p-ethylphenol, 1.79 mol% phenol and 1.01 mol% p-cresol was obtained from the reflux zone attached to the extraction tower.

EXAMPLE 5

Separation and purification of vinylphenol were carried out in accordance with the system shown in FIG. 6.

An extracting material of the same composition as used in Example 4 was fed into the central part of the extraction tower so that the rate of all the phenols fed was 0.099 mol./hr. This extraction tower had the same structure as that of the extraction tower used in Example 2 with the same inside diameter and length. A 0.512N aqueous solution of sodium hydroxide was fed at a rate of 240 ml./hour to a position 10 cm below the top of the extraction tower, and the interface between the oil phase and the aqueous phase was maintained at a position 10 cm above the bottom of the extraction tower. The aqueous phase was withdrawn from the bottom of the tower, and fed to a position 60 cm below the top of the reflux zone. This reflux zone had the same structure and size as those of the above extraction tower. Toluene was fed at a rate of 210 ml./hour to a position 10 cm above the bottom of the reflux zone; a 0.76 N aqueous solution of sodium bicarbonate, at a rate of 240 ml./hour into a position 60 cm below the top of the reflux zone; and water, at a rate of 8.4 liters/hour was fed to a position 10 cm below the top of the reflux zone. The interface between the oil phase and the aqueous phase was maintained at a position 10 cm below the top of the reflux zone. The aqueous phase was withdrawn from the bottom of the reflux zone, and the organic phase was withdrawn from the top of the reflux zone. The organic phase was fed as a total reflux to a position 10 cm above the bottom of the extraction tower. After performing the above total reflux procedure for 5 hours, the extracting procedure was continued for an additional 5 hours while adjusting the reflux ratio to 1.9. During this time, 380 ml. of toluene solution containing 98.8 mol% of p-vinylphenol, 0.37 mol% of p-ethylphenol, 0.30 mol% of phenol and 0.51 mol% of p-cresol was obtained as an extract withdrawn from the system from the reflux section.

All of the above operations were carried out at 5° C. under stmospheric pressure.

EXAMPLE 6

The separation and purification of vinylphenol were carried out in accordance with the system shown in FIG. 7.

A mixture of 16.7 wt% p-vinylphenol, 35.5 wt% p-ethylphenol, 1.0 wt% m-ethylphenol, 0.8 wt% o-ethylphenol, 1.5 wt% p-tert.-butylphenol, 1.6 wt% vinylphenol polymer and 42.9 wt% methanol was fed at the rate of 951.7 g/hr through line 1 and toluene was fed at the rate of 4034 g/hr through line 3 into the center portion of an extraction tower having an inner volume of about 10 liters and equipped with stirrers. An aqueous alkali solution containing 2.6 wt% sodium hydroxide and 2.0 wt% methanol was fed at the rate of 552 g/hr to the upper part of the extraction tower through line 4 and at the rate of 50 g/hr to the lower part of the extraction tower through line 5, and the separation and purification of p-vinylphenol were carried out. The alkali aqueous solution (extract) containing alkali salt of p-vinylphenol was continuously withdrawn from the extraction tower and fed into a reflux zone. The extract was brought into contact with toluene from line 11 and carbon dioxide gas from line 10 to remove precipitated vinylphenol polymers are fed into a separator. An aqueous solution separated in the separator was fed into the recovery tower and was brought into contact with toluene fed at the rate of 3936 g/hr from line 19. A toluene phase obtained was continuously recycled to the relux zone through line 11. On the other hand, the toluene phase containing p-vinylphenol separated from the separator was recycled with the entire amount as a reflux fraction to the extraction tower during 4 hours from the start of the extraction operation. Thereafter, 70 wt% of the toluene phase was recycled to the extraction tower and the remainder of 30 wt% was withdrawn out of the system as a product. The product was a toluene solution (toluene content 90 wt%) containing 99.1% by weight of p-vinylphenol and 0.9% by weight of ethylphenols.

The above continuous extraction operation was conducted for 240 hours, but no formation of scale was observed on the inner wall of the extraction tower and line 8.

COMPARISON EXAMPLE

The procedure of Example 6 was repeated except that no methanol was added to the starting crude vinylphenol and the alkali aqueous solution. A toluene solution of p-vinylphenol having the same purity (99.1 wt%) as in Example 6 was obtained as a product. However, for 60 hours after the extraction operation a large amount of scale deposited on the inner wall of the extraction tower and line 8, and, as a result, it was impossible to further continue the operation.

EXAMPLE 7

The procedure of Example 6 was repeated except that a mixture of 15.6 wt% p-vinylphenol, 0.7 wt% o-ethylphenol, 0.9 wt% m-ethylphenol, 33.3 wt% p-ethylphenol, 1.4 wt% p-tert.-butylphenol, 1.1 wt% vinylphenol polymer and 47.0 wt% ethanol was fed at the rate of 977.7 g/hr through line 1 and an aqueous alkali solution containing 2.6 wt% sodium hydroxide and 4.0 wt% ethanol was fed at the rate of 5611 g/hr through line 4 and at the rate of 50 g/hr through line 5 into the extraction tower. A product obtained was a toluene solution (toluene content 89.8 wt%) containing 99.3% by weight of p-vinylphenol and 0.7% by weight of ethylphenols. No formation of scale was observed even in the operation for 240 hours.

While the invention has been described in detail and with reference to specific embodiments thereof, it will be apparent to one skilled in the art that various changes and modifications can be made therein without departing from the spirit and scope thereof.

What is claimed is:

1. A process for purifying crude vinylphenol containing
   (a) vinylphenol,
   (b) impurities more acidic than vinylphenol comprising phenol and carboxylic acids, and/or
   (c) impurities less acidic than vinylphenol comprising alkylphenols having 1 to 4 carbon atoms in the alkyl group thereof, which comprises subject said crude vinylphenol at least once to an alkali extraction comprising countercurrently contacting at a temperature of from −10° to +40° C the crude vinylphenol with an aqueous alkali solution having a concentration of about 0.05 to 3 normal in an amount sufficient for extraction of only vinylphenol and/or impurities more acidic than vinylphenol together with an organic solvent having solubility in water of below 8g/100g $H_2O$ at 20° C and capable of dissolving the individual components of the crude vinylphenol and selected from the group consisting of benzene, toluene, xylene, ethylbenzene, tetralin, diethyl ether, dipropyl ether, di-sec butyl ether, dibenzyl ether, benzyl ethyl ether, amyl alcohol, hexanol, heptanol, cyclohexanol, benzyl alcohol, nitromethane, courmarone, nitropropane, nitrobenzene, o-nitrotoluene, chlorobenzene, bromobenzene, (o—, m—, p—)-chlorotoluene, chloronaphthalene, tetrachloroethane, tirchloropropane, trichlorotrifluoroethane, benzontrile, tolunitrile, 2,4-dimethylbenzonitrile, 4-isopropyl benzonitrile, butyronitrile, capronitrile, dibutyl sulfoxide, methyl phenyl sulfoxide, ethyl tolyl sulfone, butyl tolyl sulfone, dibutyl sulfone, ethyl isobutyl sulfone and a mixture containing at least one of these solvents, the amount of said organic solvent being from 1 to 100 times by weight based on the weight of the crude vinylphenol, whereby in each one of the at least one alkali extraction steps vinylphenol is separated from at least some of the impurities.

2. The process of claim 1, wherein said alkali is used in an amount of from 1.01 to 100 moles per 1 mole of components contained in the crude vinylphenol and to be extracted.

3. The process of claim 1, wherein said alkali extraction is conducted in the presence of an water-soluble alcohol to prevent a formation of scale on an inner wall of an extraction apparatus.

4. The process of claim 3, wherein said water-soluble alcohol has 1 to 4 carbon atoms.

5. The process of claim 3, wherein said water-soluble alcohol is used in an amount of from 0.5 to 50% by weight based on the weight of the aqueous alkali solution.

6. The process of claim 1, including prior to said alkali extraction, subjecting said crude vinylphenol to a water washing comprising countercurrently contacting the crude vinylphenol with water together with an organic solvent having solubility in water of below 8g/100g $H_2O$ at 20° C and capable of dissolving the individual components of the crude vinylphenol and selected from the group consisting of an aromatic hydrocarbon, an ether, an alcohol, a nitro compound, a halogenated hydrocarbon, a nitrile, a sulfone, a sulfoxide and a mixture containing at least one of these compounds.

7. The process of claim 6, wherein said water washing and said alkali extraction are performed at a temperature from 0° to 40° C.

8. The process of claim 1, including after said alkali extraction subjecting a fraction containing vinylphenol obtained from the alkali extraction to a water washing comprising countercurrently contacting said fraction with water together with an organic solvent having solublity in water of below 8g/100g $H_2O$ at 20° C and capable of dissolving the individual components of the crude vinylphenol and selected from the group consisting of an aromatic hydrocarbon, an ether, an alcohol, a nitro compound, a halogenated hydrocarbon, a nitrile, a sulfone, a sulfoxide and a mixture containing at least one of these compounds.

9. The process of claim 8, wherein said alkali extraction and said water washing are performed at a temperature from 0° to +40° C.

10. The process of claim 1, comprising subjecting said crude vinylphenol once to said alkali extraction.

11. The process of claim 10, including prior to said alkali extraction, subjecting said crude vinylphenol to a water washing comprising countercurrently contacting the crude vinylphenol with water together with an organic solvent having solubility in water of below 8g/100g $H_2O$ at 20° C and capable of dissolving the individual components of the crude vinylphenol and selected from the group consisting of an aromatic hydrocarbon, an ether, an alcohol, a nitro compound, a halogenated hydrocarbon, a nitrile, a sulfone, a sulfoxide and mixture containing at least one of these compounds.

12. The process of claim 10, including after the alkali extraction, subjecting a fraction containing vinylphenol and obtained from the alkali extraction to a water washing comprising contacting countercurrently said fraction with water together with an organic solvent having solubility in water of below 8g/100g $H_2O$ at 20° C and capable of dissolving the individual components of the crude vinylphenol and selected from the group consisting of an aromatic hydrocarbon, an ether, an alcohol, a nitro compound, a halogenated hydrocarbon, a nitrile, a sulfone, a sulfoxide and a mixture containing at least one of these compounds.

13. The process of claim 1, comprising subjecting said crude vinylphenol to said alkali extraction twice, wherein the crude vinylphenol is subjected to a first alkali extraction, and then a fraction containing vinylphenol and resulting from said first alkali extraction is subjected to a second alkali extraction.

14. The process of claim 1, wherein said organic solvent is benzene, toluene, xylene, ethylbenzene, tetralin or mixtures thereof.

15. The process of claim 1, wherein said organic solvent is diethyl ether, dipropyl ether, di-sec. butyl ether, dibenzyl ether, benzyl ethyl ether, courmarone or mixtures thereof.

16. The process of claim 1, wherein said organic solvent is amyl alcohol, hexanol, heptanol, cyclohexanol, benzyl alcohol or mixtures thereof.

17. The process of claim 1, wherein said organic solvent is nitromethane, nitropropane, nitrobenzene, o-nitrotoluene or mixtures thereof.

18. The process of claim 1, wherein said organic solvent is chlorobenzene, bromobenzene, (o-, m-, p-) chlorotoluene, chloronaphthalene, tetrachloroethane, trichloropropane, trichlorotrifluoroethane or mixtures thereof.

19. The process of claim 1, wherein said organic solvent is benzonitrile, tolunitrile, 2,4-dimethylbenzonitrile, 4-isopropyl benzonitrile, butyronitrile, capronitrile or mixtures thereof.

20. The process of claim 1, wherein said organic solvent is dibutyl sulfoxide, methyl phenyl sulfoxide or mixtures thereof.

21. The process of claim 1, wherein said organic solvent is ethyl tolyl sulfone, butyl tolyl sulfone, dibutyl sulfone, ethyl isobutyl sulfone or mixtures thereof.

* * * * *